(12) United States Patent
Carroll

(10) Patent No.: US 8,790,686 B2
(45) Date of Patent: Jul. 29, 2014

(54) METHOD AND COMPOSITION FOR TREATING HEMORRHOIDS

(76) Inventor: L. Gaye Carroll, Magnolia, AR (US)

(*) Notice: Subject to any disclaimer, the term of this patent is extended or adjusted under 35 U.S.C. 154(b) by 1999 days.

(21) Appl. No.: 11/106,059

(22) Filed: Apr. 14, 2005

(65) Prior Publication Data

US 2006/0008481 A1     Jan. 12, 2006

Related U.S. Application Data

(63) Continuation-in-part of application No. 10/424,394, filed on Apr. 28, 2003, now abandoned, which is a continuation-in-part of application No. 10/190,718, filed on Oct. 10, 2002, now abandoned.

(51) Int. Cl.
| | | |
|---|---|---|
| *A61K 9/02* | (2006.01) | |
| *A61K 9/06* | (2006.01) | |
| *A61K 47/44* | (2006.01) | |
| *A61K 9/00* | (2006.01) | |
| *A61K 31/136* | (2006.01) | |

(52) U.S. Cl.
CPC .............. *A61K 47/44* (2013.01); *A61K 9/0031* (2013.01); *A61K 9/02* (2013.01); *A61K 9/06* (2013.01); *A61K 31/136* (2013.01)
USPC ............ 424/436; 424/400; 424/404; 424/434

(58) Field of Classification Search
CPC ....................................................... A61K 31/13
See application file for complete search history.

(56) References Cited

U.S. PATENT DOCUMENTS

| | | | | |
|---|---|---|---|---|
| 3,812,250 | A | * | 5/1974 | Aubert et al. ................. 424/659 |
| 4,626,433 | A | * | 12/1986 | Gros ............................. 424/682 |
| 4,657,691 | A | * | 4/1987 | Hara et al. ................. 15/104.93 |
| 4,746,675 | A | | 5/1988 | Makino et al. |
| 4,891,356 | A | | 1/1990 | Szabo |
| 5,709,672 | A | * | 1/1998 | Illner ............................ 604/265 |
| 6,242,010 | B1 | | 6/2001 | Hersh |

FOREIGN PATENT DOCUMENTS

| | | | |
|---|---|---|---|
| JP | 55-040644 | | 3/1980 |
| JP | 04-091036 | | 3/1992 |
| JP | 04091036 | A * | 3/1992 |
| JP | 10-218780 | | 8/1998 |
| RU | 2124362 | | 1/1999 |
| WO | 0128515 | | 4/2001 |

OTHER PUBLICATIONS

Decision of Refusal, Japanese Patent Office, Mar. 2, 2012 (translation).
Gloor, M., Wolnicki, D., Anti-irritative effect of methylrosaniline chloride (Gentian violet), Dermatology, 2001, p. 325-328, vol. 203 (4) (abstract).
PCT International Search Report, Oct. 23, 2003.
PCT Written Opinion, Jun. 22, 2004.
PCT International Preliminary Examination Report, Dec. 13, 2004.
First Examination Report, Indian Patent Office, Jun. 4, 2006.
Letter from Indian Patent Office, Jan. 18, 2007.
Letter from Indian Patent Office, May 29, 2007.
Notification of Reasons for Refusal, Japanese Patent Office, Mar. 10, 2009.
Decision of Refusal, Japanese Patent Office, Jul. 7, 2009.
Notice of Request for Submission of Argument, Korean Intellectual Property Office, Jun. 15, 2007 (translation).
Notice of Request for Submission of Argument, Korean Intellectual Property Office, Oct. 23, 2007 (translation).
Notice of Decision to Grant Patent, Korean Intellectual Property Office, Nov. 16, 2007.
Office Action, European Patent Office, Jul. 6, 2009.
Office Action, Russian Patent Office, Mar. 14, 2006.
Russian Patent 2,310,455 C2, Russian Patent Office (Inventor: Gaye Carroll), Jan. 10, 1999.
Notification of the First Office Action, Patent Office of the People's Republic of China, Mar. 10, 2006.
Notification of the Second Office Action, Patent Office of the People's Republic of China, Oct. 13, 2006.
Certificate of Invention Patent, Patent Office of the People's Republic of China, Feb. 27, 2008.
Office Action, Canadian Patent Office, Oct. 26, 2007.
Amendments/Remarks After Examiners Report, Canadian Patent Application No. 2,498,457, Feb. 13, 2008.
Response to Office Action of European Patent Office, Sep. 21, 2009.
Response to the Indian Patent Office, Sep. 28, 2006.
Response to the Notification of Reasons for Refusal of the Japanese Patent Office, Jun. 5, 2009.
Response to Notice of Request for Submission of Argument from the Korean Intellectual Property Office, Jul. 25, 2007.
Certificate and Patent Specification from European Patent Office (Nov. 16, 2011).

\* cited by examiner

*Primary Examiner* — Lakshmi Channavajjala
(74) *Attorney, Agent, or Firm* — Richard Blakely Glasgow

(57) ABSTRACT

A hemorrhoid-treating composition comprising gentian violet and a lubricant or suppository base. A method of treating hemorrhoids by topically applying a composition comprising gentian violet and a lubricant or suppository base.

5 Claims, No Drawings

METHOD AND COMPOSITION FOR TREATING HEMORRHOIDS

CROSS-REFERENCE TO RELATED APPLICATIONS

This application is a continuation-in-part of application Ser. No. 10/424,394, filed Apr. 28, 2003 now abandoned, which is a continuation-in-part of application Ser. No. 10/190,718, filed Oct. 10, 2002 now abandoned.

STATEMENT REGARDING FEDERALLY SPONSORED RESEARCH OR DEVELOPMENT

Not applicable

BACKGROUND OF THE INVENTION

1. Field of the Invention

The present invention relates to a composition which is particularly useful in the treatment of hemorrhoids. More particularly, the present invention relates to a hemorrhoid-treating composition which includes an ointment mixture of the antiseptic/bactericide/fungicide/anthelmintic gentian violet (methylrosaniline) and a lubricant such as petroleum jelly, also known as petrolatum or mineral jelly. The composition further includes a suppository. The composition imparts a soothing and healing effect on swollen hemorrhoids, and particularly, on bleeding hemorrhoids.

2. Background of the Invention

Hemorrhoids are swollen blood vessels in the rectum. There are two basic types of hemorrhoids: internal and external. Internal hemorrhoids are swollen and inflamed veins far up in the rectum. Internal hemorrhoids cannot be seen or felt and usually are not painful due to the paucity in nerve endings in the upper portion of the rectum. While internal hemorrhoids are most commonly manifested by anal bleeding, they may prolapse, or protrude outside the anal sphincter. Usually, prolapsed internal hemorrhoids may be gently pushed back into place in the rectum.

External hemorrhoids are swollen blood vessels in the anus and are usually manifested by pain as well as bleeding. When external hemorrhoids prolapse, or protrude from the anal sphincter, blood clots sometimes form, causing an extremely painful condition known as thrombosis. While they usually disappear by themselves within about a week, thrombosed hemorrhoids may be removed by a physician or may be treated with a pain-reducing medication to reduce the pain.

It is believed that hemorrhoids are caused by the exertion of abdominal pressure on rectal veins, causing the veins to swell and become irritated. The abdominal pressure may be caused by a variety of factors and conditions including obesity, pregnancy, prolonged standing or sitting, liver disease, straining during bowel movements, coughing, sneezing, vomiting or holding the breath during physical activity. Hemorrhoids are largely preventable by the adoption of a high-fiber diet. On the other hand, persons whose diet consists largely of low-fiber, processed foods tend to run the highest risk of developing hemorrhoids. Furthermore, inadequate fluid intake can contribute to the development of hemorrhoids by causing the development of hard stools which irritate and inflame the rectal veins.

About half of persons living in the United States will be afflicted with hemorrhoids at some point during their lives. Hemorrhoids most often strike persons between the ages of 20 and 50. Some evidence indicates that "weak" veins, which are most susceptible to developing hemorrhoids, are inherited.

BRIEF SUMMARY OF THE INVENTION

The present invention is generally directed to a composition for the treatment of hemorrhoids. More particularly, the present invention relates to a hemorrhoid-treating composition which includes a mixture of the antiseptic/bactericide/fungicide/anthelmintic gentian violet (methylrosaniline) and a lubricant such as petroleum jelly, also known as petrolatum or mineral jelly. In another embodiment, the composition is prepared as a suppository using a suitable suppository base. The composition imparts a soothing and healing effect on swollen hemorrhoids, and particularly, on bleeding hemorrhoids.

DETAILED DESCRIPTION OF THE SEVERAL VIEWS OF THE DRAWINGS

Not applicable

DETAILED DESCRIPTION OF THE INVENTION

The present invention includes a composition for the treatment of hemorrhoids, particularly external hemorrhoids. The composition is easy to apply and promotes pain reduction, as well as healing, of the hemorrhoids, including inflammation and torn tissue associated with hemorrhoids. In a preferred embodiment, the composition includes an ointment mixture of gentian violet (methylrosaniline) which is thoroughly mixed with a lubricant such as petroleum jelly, also known as petrolatum or mineral jelly. The methylrosaniline is an effective antiseptic, bactericide, fungicide and anthelmintic which prevents or fights infection and reduces pain. The lubricant provides a vehicle for effective delivery of the methylrosaniline to the inflamed hemorrhoid tissue. In a typical embodiment, the composition includes about seven (7) drops of the liquid methylrosaniline antiseptic/bactericide/fungicide/anthelmintic, per teaspoon of the lubricant. The antiseptic/bactericide/fungicide/anthelmintic may be dispensed from a medicine dropper such as an EZY CARE (trademark) straight-tip or bent-tip, glass medicine dropper available from Apothecary Products, Inc. of Minneapolis, Minn. The EZY CARE (trademark) medicine dropper has a capacity of 1 ml of liquid, or approximately 30-35 drops. Accordingly, in a preferred: embodiment the composition mixture includes at least about 0.2 ml to about 0.3 ml of the methylrosaniline per teaspoon of lubricant. However, it is understood that other types of medicine droppers may be used to dispense the drops into the lubricant. After the methylrosaniline is added to the lubricant, the two components are thoroughly mixed until the composition mixture assumes the substantially homogenous violet color of the methylrosaniline. After formation, the composition is typically placed in a typically 6 oz. capped, plastic applicator tube for subsequent application.

In another embodiment, the composition is prepared in the form of a suppository using a suitable suppository vehicle or base. The suppository base is glycerinated gelatin, although alternative suppository bases, including cocoa butter and polyethylene glycol, in non-exclusive particular, may be used. The active ingredient antiseptic/bactericide/fungicide/anthelmintic gentian violet (methylrosaniline) is added to the suppository base in a quantity of typically at least about 0.2 ml to about 0.3 ml of gentian violet (methylrosaniline) per teaspoon of suppository base. The methylrosaniline may be dispensed from a medicine dropper such as an EZY CARE (trademark) straight-tip or bent-tip, glass medicine dropper available from Apothecary Products, Inc. of Minneapolis, Minn., for example. The therapeutic quantity of methylrosaniline equates to typically at least about seven (7) drops of the methylrosaniline per teaspoon of suppository base. The methylrosaniline is then thoroughly' mixed with the suppository base to obtain a substantially homogenous suppository mixture. One teaspoon of the suppository mixture may be formed or shaped into suppositories each having dimensions of typically about 0.25 inch in diameter and 1.5 inch in length, with a tapered end for anal insertion of the suppository. In that case, each suppository typically has at least about 2-4 drops of the methylrosaniline. However, it is understood that the suppository may be shaped into suppositories having any suitable dimensions. and shape.

One possible method of applying the ointment composition to the inflamed hemorrhoidal tissue includes dispensing the composition from a typically b-ounce, capped plastic tube. A replaceable applicator cap having a smooth, rounded applicator tip may be provided on the capped tube for applying the composition to the hemorrhoids in the anal area. Preferably, the applicator tip is ¾" long, and the top of the 6-ounce tube, as well as the base of the applicator tip, is ¼" in diameter. The applicator tip tapers from the ¼" base to the ⅛" tip thereof. Applicator openings are provided in the sides of the applicator tip for dispensing the composition from the tip to the inflamed hemorrhoidal tissue.

It is understood that the tube and applicator cap heretofore described represent only one example of storage and application of the composition. Accordingly, the composition may be stored in any type of suitable container for subsequent application, and may be applied through the applicator cap heretofore described or through any other type of applicator or other instrument suitable for the purpose. The composition may also be applied manually to the inflamed area. Furthermore, the fingers of the patient afflicted with prolapsed hemorrhoids may lubricate his or her fingers with the composition mixture and use the lubricated fingers to gently push the prolapsed hemorrhoidal tissue back into the anal canal. The composition mixture reduces hemorrhoidal pain and promotes healing of the inflamed hemorrhoidal tissue.

The invention will be better understood by consideration of the following examples.

Example 1

A composition mixture was prepared by dropping seven (7) drops of gentian violet (methylrosanaline) antiseptic/bactericide/fungicide/anthelmintic, using an EZY CARE (trademark) medicine dropper, into one (1) teaspoon of petroleum jelly and then thoroughly mixing the methylrosanaline with the petroleum jelly until the resulting composition mixture assumed the substantially homogenous violet color of the methylrosaniline. The composition mixture was placed in 6-ounce capped tube having an applicator cap for subsequent application of the composition to inflamed hemorrhoidal tissue.

Example 2

The composition mixture prepared according to EXAMPLE 1 above was applied to the inflamed hemorrhoidal tissue of a patient using the applicator cap on the tube. The composition mixture was applied as often as necessary to relieve pain. The composition mixture significantly reduced pain associated with the hemorrhoids and promoted healing of the inflamed hemorrhoidal tissue.

Example 3

A patient afflicted with inflamed hemorrhoids applied the composition mixture prepared according to EXAMPLE 1 to the patient's inflamed hemorrhoidal tissue using the patient's fingers. The composition mixture was applied as often as necessary to relieve pain. The composition mixture significantly reduced pain associated with the hemorrhoids and promoted healing of the inflamed hemorrhoidal tissue.

Example 4

A patient afflicted with prolapsed hemorrhoids lubricated the patient's fingers using the composition mixture prepared according to EXAMPLE 1 above. The patient used the lubricated fingers to gently push the prolapsed hemorrhoids back into the patient's anal canal. The composition applied in this manner instantly alleviated pain associated with the hemorrhoids and promoted healing of the inflamed hemorrhoidal tissue.

Example 5

Suppositories were prepared by dropping seven (7) drops of gentian violet (methylrosanalnne) antiseptic/bactericide/fungicide/anthelmintic, using an EZY CARE (trademark) medicine dropper, into one (1) teaspoon of glycerinated gelatin and then thoroughly mixing the methylrosanaline with the glycerinated gelatin until the resulting suppository mixture was substantially homogenous. The suppository mixture was shaped into two (2) suppositories for subsequent anal insertion to treat inflamed hemorrhoidal tissue.

Example 6

A suppository prepared according to EXAMPLE 5 above was applied by anal insertion to inflamed hemorrhoidal tissue of a patient. The suppositories were applied as often as necessary to relieve pain. The suppositories significantly reduced pain associated with the hemorrhoids and promoted healing of the inflamed hemorrhoidal tissue.

The present invention is further directed to a method of treating the symptoms and causes of venous or tissue infestations, inflammations and infections associated with hemorrhoids or other conditions. The method includes applying a composition which includes gentian violet and a suppository base to the afflicted tissues in a pharmaceutically effective quantity sufficient for, but not limited to, oral, vaginal, urethral or rectal use.

The present invention is further directed to a method of treating symptoms and causes of infestations, inflammations, infections and swollen and ruptured veins. According to the method, a composition which includes gentian violet and petroleum jelly or other suitable lubricant is applied to the swollen and ruptured veins.

The present invention is further directed to a method of topically treating and alleviating excruciating pain of a thrombus or tissue and veins expelled from an anal canal through the pressure and strain associated with alterations in defecation patterns. According to the method, a composition which includes gentian violet and a lubricant base is digitally or otherwise applied to the thrombus or tissue and veins. The expelled tissue and veins are then digitally or otherwise pushed back into the anal canal, after which a pharmaceutically effective quantity of the composition is applied to the tissue and veins to promote healing of the tissue and veins through reduced infestations, inflammation and infection.

The invention is further directed to a method of preventing enlarged or dilated veins from being expelled from an anal canal through the strain and stress associated with alterations in defecation patterns and preventing or reducing septic and toxic infestations, inflammations and infections. According to the method, a composition which includes gentian violet and a carrier such as a suppository or lubricant base is applied in a pharmaceutically effective quantity to the enlarged or dilated veins prior to defecation. The composition eliminates or reduces swelling and inflammation of the veins, thus preventing or reducing prolapse of the veins from the anal canal as a result of defecation.

In the various methods, the gentian violet may be present in the composition in a concentration of at least about 1 part of the gentian violet per about 11 parts of the composition by weight, or at least about 0.0032 ounces of gentian violet per gram (0.035 ounces) of the composition. The suppository base or lubricant may be present in the composition in a concentration of about 0.0318 ounces or less per gram of the composition. The suppository base may be a hydrogenated vegetable oil base, polyethylene glycol, glycerinated gelatin or any suitable water-soluble or oil-soluble base. The lubricant may be petroleum jelly or any other suitable lubricant. Furthermore, the composition is suitable for, but not limited to, oral, vaginal, urethral or rectal use. For example, the composition may be formed into a tablet and swallowed to treat the causes and symptoms associated with the inflammation of veins or tissues in the digestive tract.

While the preferred embodiments of the invention have been described above, it will be recognized and understood that various modifications can be made in the invention and the appended claims are intended to cover all such modifications which may fall within the spirit and scope of the invention.

The invention claimed is:

1. A method of treating hemorrhoids by topically applying a composition of matter comprising gentian violet and a pharmaceutically acceptable vehicle, wherein the percentage of gentian violet is at least 9.1% by weight of the composition, and said pharmaceutically acceptable vehicle is no greater than 90.9% by weight of the composition and is selected from the group consisting of a lubricant and a suppository base.

2. The method of claim 1, wherein said suppository base is selected from one of hydrogenated vegetable oil base, cocoa butter, polyethylene glycol, glycerinated gelatin, a water-soluble base, or an oil-soluble base.

3. The method of claim 1, wherein said lubricant is petroleum jelly.

4. The method of claim 1, wherein said pharmaceutically acceptable vehicle is said lubricant, further comprising digitally returning exposed tissue and veins to the anal canal wherein said pharmaceutically acceptable vehicle is said lubricant.

5. The method of claim 1, wherein said pharmaceutically acceptable vehicle is said lubricant, further comprising dispensing said composition of matter from a plastic tube with an applicator tip wherein said pharmaceutically acceptable vehicle is said lubricant.

* * * * *